United States Patent [19]

Tower

[11] Patent Number: 4,913,701
[45] Date of Patent: Apr. 3, 1990

[54] BALLOON CATHETER AND METHOD OF MANUFACTURING THE SAME

[75] Inventor: Allen J. Tower, N. Lawrence, N.Y.

[73] Assignee: NuMed, Inc., Hopkinton, N.Y.

[21] Appl. No.: 254,198

[22] Filed: Oct. 6, 1988

[51] Int. Cl.[4] .............................................. A61M 29/02
[52] U.S. Cl. ..................................... 604/103; 29/447; 606/192
[58] Field of Search ............. 604/103; 128/344, 348.1, 128/DIG. 18; 29/447

[56] References Cited

U.S. PATENT DOCUMENTS

| | | |
|---|---|---|
| 3,634,924 | 1/1972 | Blake et al. . |
| 3,837,347 | 9/1974 | Tower . |
| 3,901,965 | 8/1975 | Honeyman, III . |
| 4,003,382 | 1/1977 | Dyke . |
| 4,055,187 | 10/1977 | Patel et al. . |
| 4,251,305 | 2/1981 | Becker et al. . |
| 4,301,803 | 11/1981 | Handa et al. . |
| 4,323,071 | 4/1982 | Simpson et al. ............ 128/343 |
| 4,342,316 | 8/1982 | Rosenberg . |
| 4,406,653 | 9/1983 | Nunez . |
| 4,445,891 | 5/1984 | Patel . |
| 4,624,657 | 11/1986 | Gould et al. . |
| 4,661,095 | 4/1987 | Taller et al. . |
| 4,702,252 | 10/1987 | Brooks et al. . |
| 4,737,219 | 4/1988 | Taller et al. . |

Primary Examiner—Michael H. Thaler
Attorney, Agent, or Firm—Wall and Roehrig

[57] ABSTRACT

A balloon catheter that includes an elongated cylindrical body having a distal end and a proximal end, a first reduced diameter section and a second further reduced diameter section which, in the preferred embodiment of the invention, forms a tip at the distal end of the catheter. The balloon is bonded to the distal end of the catheter so as to enclose the reduced diameter sections. The balloon is made from a tube of thermosetting polyurethane and includes a pair of end cuffs and an inflatable bag centrally located between the cuffs. One cuff is bonded to the tip of the catheter with the end face of the cuff facing a shoulder formed between the tip and the adjacent first reduced diameter section. The balloon is everted over the bonded cuff and the opposing cuff is bonded to the first reduced diameter section so that its end face faces a shoulder formed between the first reduced diameter section and the body of the catheter. An air lumen communicates with the bag via a port formed in the wall of the first reduced section. When deflated, the balloon is completely retracted below the outside surface of the catheter body. The cuffs of the balloon are bonded to the catheter using both an adhesive bond and a thermal bond.

7 Claims, 2 Drawing Sheets

BALLOON CATHETER AND METHOD OF MANUFACTURING THE SAME

BACKGROUND OF THE INVENTION

This invention relates to a balloon catheter and, in particular to a process for mounting a polyurethane balloon on a polyethylene catheter.

Polyethylene is generally the preferred material for use in catheters because it will retain all of its desirable characteristics at body temperature and it is non-toxic. It is, however, difficult to bond most balloons to polyethylene. Certain processes have been developed by which latex balloons can be safely secured to polyethylene catheters. Latex, however, ages rapidly, particularly in the presence of light. Most cathers are packaged in clear plastic trays for sanitary and safety reasons, and as a consequence, those devices utilizing latex balloons have a very short shelf-life. Polyurethane balloons have been developed that overcome the storage problems associated with their latex counterparts. As described in U.S. Pat. No. 4,661,095, polyurethane ballons can be securely bonded to catheters formed of thermoplastic polyurethane using special polyurethane adhesives. Although polyurethane catheters work well in practice, they nevertheless do not provide all of the desirable characteristics demanded by many physicians.

One method of securing a balloon to a catheter is to tightly wrap the ends of the balloon with a fine thread or suture to provide a seal between the balloon and the catheter. This type of mechanical bond avoids many problems associated with adhesives, but usually requires that a metal ferule be placed under the windings to prevent the balloon from collapsing after inflation. These devices, therefore, are difficult to manufacture and generally increase the overall diameter of the catheter. A second method of bonding a balloon to a catheter is by stretching the ends of the balloon over the catheter and applying an adhesive to the junction between the balloon and the cather at both ends of the balloon. The adhesive is allowed to "wick" under the ends of the balloon by capillary action and thus sealing the joint. Typically, the adhesive will penetrate the joint to varying depths thereby resulting in uneven bonding. Control over the quality of the product is therefore difficult to maintain.

SUMMARY OF THE INVENTION

It is therefore an object of the present invention to improve balloon catheters.

It is a further object of the present invention to provide a balloon catheter wherein the balloon is completely retracted beneath the outer surface of the catheter when the balloon is deflated to provide for ease of insertion into a blood vessel or the like.

A still further object of the present invention is to securely bond a polyurethane balloon to a polyethylene catheter.

Another object of the present invention is to provide a method for double bonding a balloon to a catheter.

Yet another object of the present invention is to provide for greater patient safety during procedures and/or involving the use of a balloon catheter.

These and other objects of the present invention are attained by means of a balloon catheter that includes an elongated cylindrical body having a distal end and a proximal end, a first reduced diameter section and a second further reduced diameter section which, in the preferred embodiment of the invention, forms a tip at the distal end of the catheter. The balloon is bonded to the distal end of the catheter so as to enclose the reduced diameter sections. The balloon is made from a tube of thermosetting polyurethane and includes a pair of end cuffs and an inflatable bag centrally located between the cuffs. One cuff is bonded to the tip of the catheter with the end face of the cuff facing a shoulder formed between the tip and the adjacent first reduced diameter section. The balloon is everted over the bonded cuff and the opposing cuff is bonded to the first reduced diameter section so that its end face faces a shoulder formed between the first reduced diameter section and the body of the catheter. An air lumen communicates with the bag via a port formed in the wall of the first reduced section. When deflated, the balloon is completely retracted below the outside surface of the catheter body. The cuffs of the balloon are bonded to the catheter using both an adhesive bonding means and a thermal bonding means.

BRIEF DESCRIPTION OF THE DRAWINGS

For a better understanding of these and other objects of the present invention, reference is made to the following detailed description of the invention which is to be read in association with the accompanying drawings, wherein.

DETAILED DESCRIPTION OF THE INVENTION

Turning now to the drawings, there is illustrated a manufacturing process for securely joining a polyurethane balloon to the body of a polyethylene catheter. As noted above, bonding most balloon materials to polyethylene catheters has been generally difficult when using conventional joining techniques. As will be explained in greater detail below, the present process results in the formation of a double bond between the balloon and the catheter to provide for proper sealing and thus inflation of the balloon. It also results in the manufacture of a device wherein the balloon, when deflated, is completely retracted in a stored position below the outer surface of the catheter.

Figure 1:
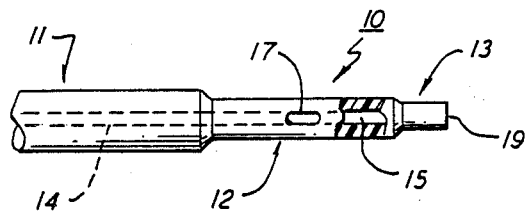
FIG. 1 is a partial side elevation showing the distal end of a catheter used in the practice of the present invention with a portion broken away to show the main lumen contained therein.

As best seen in FIG. 1, the catheter includes a cylindrical body 11 that is necked down at its distal end to form a first reduced diameter section 12 and a second reduced diameter section 13 which, in this embodiment, forms the distal tip of the catheter. At least two lumens are mounted as an integral part of the catheter body inside the catheter body. These include an air lumen 14 and a drainage or main lumen 15. The air lumen is connected to an inflation port 17 that passes through the side wall of the first reduced section 12. The opposite end of the air lumen passes out of the proximal end of the catheter and is connectable to a syringe or the like (not shown), the use of which will become apparent from the disclosure below. The main lumen 15 passes axially through the catheter and opens to the outside through the end face 19 of the tip.

Figure 2:
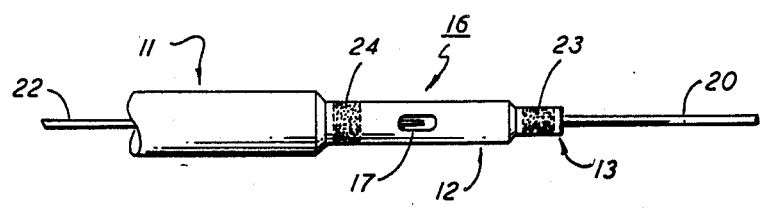
FIG. 2 is also a side elevation showing a mandrel inserted in the distal end of the catheter.

During the balloon mounting process, a mandrel 20 (FIG. 2) is passed into the main lumen through the distal end face 19. A close sliding fit is maintained between the inside surface of the lumen and the outside surface of the mandrel. A thin wire 22 is also passed from the proximal end of the catheter through the air lumen so that the forward end of the wire is situated just inside the inflation port. The wire and the mandrel keep the lumens open as the catheter goes through the various processing steps and also help prevent contaminants from entering the lumens.

Figure 3:
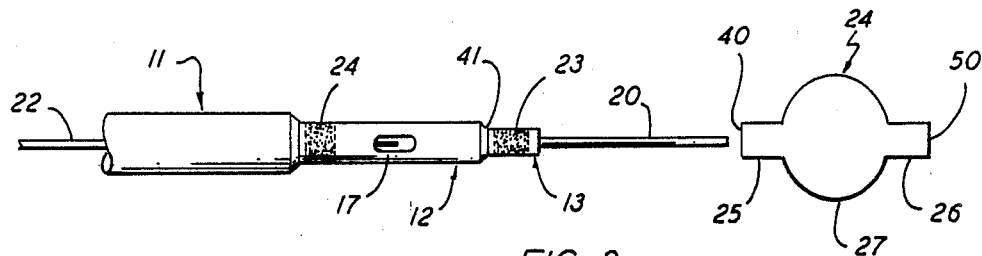
FIG. 3 shows a polyurethane balloon being slipped over the distal end of the catheter.

As illustrated in FIG. 3, the tip surface 23 and a second surface 24 at the back of the first reduced section are roughened with sand paper or the like prior to mounting the balloon.

Figure 9:
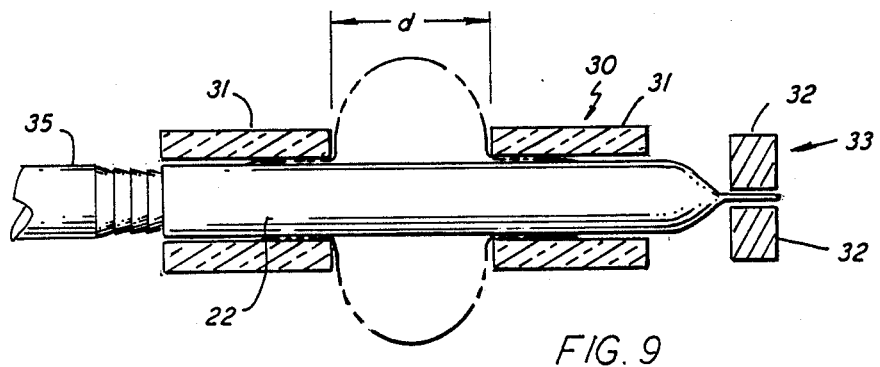
FIG. 9 illustrates the balloon being formed in a fixture from a tube of thermosetting polyurethane.

With further reference to FIGS. 3 and 9, the balloon 24 is fabricated from a thin wall sleeve 22 of polyurethane having a wall thickness of about 0.005 inches. The balloon, in finished form, has a pair of opposed cuffs 25 and 26 that are integral with a centrally located inflation bag 27. As best seen in FIG. 9, the balloon is fabricated in a fixture 30 that includes two spaced apart glass rods 31—31. The gap distance (d) between the rods is equal to the desired bag width between cuffs 25 and 26. One end of the sleeve is passed through the rods and is closed off by the jaws 32—32 of a clamping unit 33. A nozzle 35 is inserted into the opposite end of the sleeve. The section of the sleeve between the glass rods is heated by any suitable means to about 170°, while simultaneously therewith about one cubic centimeter of water is introduced into the sleeve through the nozzle. This causes the heated section of the sleeve that is situated between the rods to expand outward, as shown in phantom outline, to form a flaccid bag. After the bag has been formed, the sleeve is removed from the fixture and the cuffs cut to any suitable length.

Figure 4:
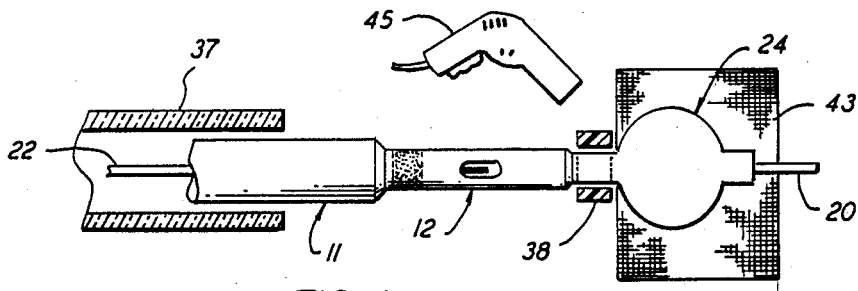
FIG. 4 illustrates one end of the balloon being thermally bonded to the tip of the catheter.

As illustrated in FIG. 4, a glass tube 37 is passed over the distal end of the catheter and moves forward toward the proximal end thereof. The inside diameter of the tube is slightly greater than the outside diameter of the catheter body 11. The tube is stored at the proximal end of the catheter until it is needed for use in a later processing step. A sleeve 38 formed of a heat shrinkable silicone (silastic) is passed onto the first recessed section 12 of the catheter and an adhesive is placed over the roughened surface 23 at the tip of the device. Cuff 25 on the balloon is passed over the tip and the free end 40 of the cuff is positioned adjacent the shoulder 41 (FIG. 3) formed between the tip 13 and the first recessed section 12. The adhesive used in this process is a cyanoacrylate material. The axial length of cuff 25 is formed so that it extends about one millimeter beyond the distal end face 19 of the catheter.

The adhesive is permitted to dry or set and the heat shrinkable sleeve is moved over the bonded cuff 25 as shown in FIG. 4. The inflation bag 27 and cuff 26 on the balloon are enclosed in a heat sink 43, which can be a wet cloth, and heat from an air gun 45 is directed at the sleeve. Under influence of the heat, the sleeve shrinks into tightening contact around the entire circumference of the cuff to apply a uniform pressure thereagainst. Heating the cuff region causes the polyurethane to shrink and the polyethylene to expand. Sufficient heat is applied to the cuff region to thermally mold the cuff to the tip of the catheter. This coupled with the adhesive bond insures that the balloon will remain securely affixed to the tip end of the catheter body during all intended examination and treatment procedures.

Figure 5:
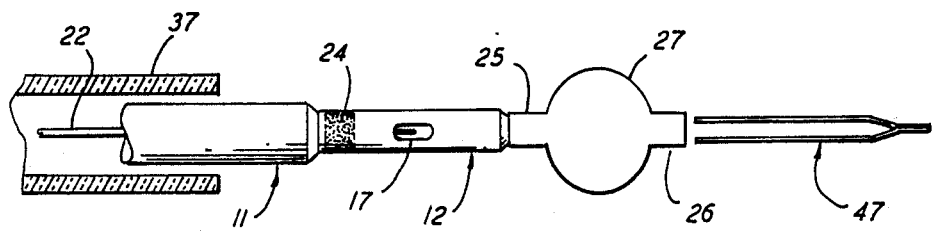
FIG. 5 shows the opposite end of the balloon being stretched to facilitate everting the balloon over the tip.
Figure 6:
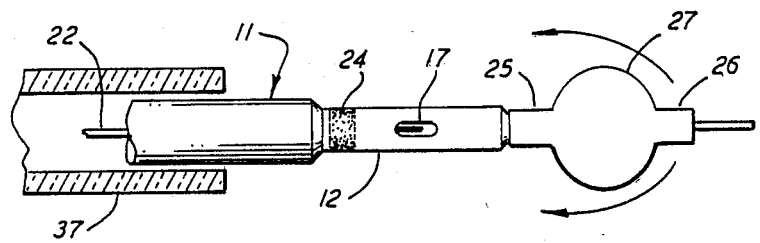
FIG. 6 shows the balloon being everted.
Figure 7:
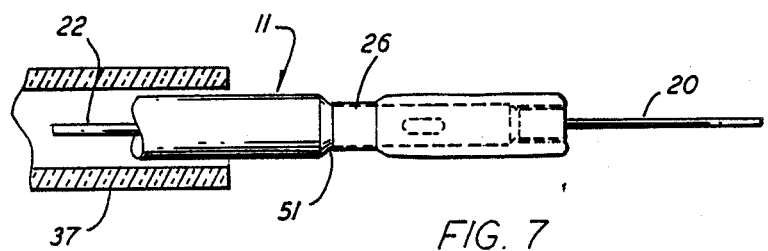
FIG. 7 shows the balloon retracted in a deflated condition below the outside surface of the catheter.

The heat sink and the heat shrinkable sleeve are removed from the distal end of the catheter along with the mandrel 20. The opening in the opposing balloon cuff 26 is now stretched using a pair of tweezers 47 (FIG. 5) so that it can pass over the first reduced section 12 of the catheter. Adhesive, as described above, is placed about the roughened surface 24 on the first recessed section and the balloon is everted over the previously bonded cuff as illustrated in FIGS. 6 and 7. Cuff 26 is passed over surface 24 and the end face 50 of the cuff is placed adjacent to the shoulder 51 connecting the recessed section 12 to the body 11 of the catheter. The mandrel 20 is also reinserted into the main lumen.

Figure 8:
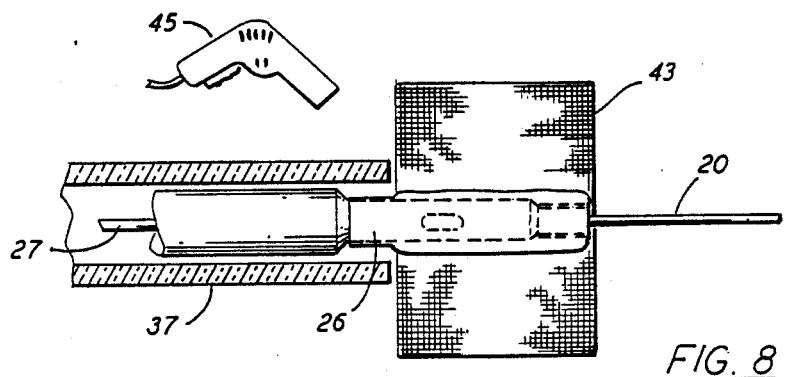
FIG. 8 illustrates the opposite end of the balloon being thermally bonded to the catheter.

The adhesive is allowed to dry, thus bonding cuff 26 to the catheter body. As illustrated in FIG. 8, the inflation bag 27 and cuff 25 are again wrapped with a wet cloth 43 and the glass tube 37 brought forward over the cuff 26. Sufficient heat is applied by air gun 45 to the tube to cause the polyethylene in the heated region below the tube to expand while at the same time causing the polyurethane cuff to shrink and become physically and thermally bonded to the catheter. As can be seen, both cuffs of the balloon are now double bonded to the catheter to insure that the balloon will remain in place when placed in use. When deflated, the inflatable bag of the balloon extends longitudinally back along the surface of the first reduced section and encircles the inflation port 17 so that it can be inflated when required.

As can be seen by this construction, the inflatable bag of the balloon can be stored in a collapsed condition against the recessed section 12 of the catheter so that it is well retracted below the outside surface of the body section 11. The bag can be collapsed by exhausting air from the bag through the inflation lumen. Accordingly, the catheter is able to be passed easily through an artery or other vessel to position the inflation bag within a desired body region where it can be inflated in a normal manner to carry out a desired task.

Although the present invention has been described with specific reference to a process for mounting a balloon in the tip of a catheter, is not necessarily limited to this specific location and the instant procedure can be employed to similarly mount the balloon anywhere along the length of the catheter body.

While this invention has been explained with reference to the structure disclosed herein, it is not confined to the details as set forth and this application is intended to cover any modifications and changes as may come within the scope of the following claims.

What is claimed is:

1. A balloon catheter that includes an elongated cylindrical catheter body formed of polyethylene and having a distal end and a proximal end, said body further including a first reduced section having a smaller diameter than said body and a second further reduced section positioned adjacent to the first reduced section toward the distal end of said body, said second reduced section having a smaller diameter than the first reduced section, a thin walled balloon formed of thermosetting polyurethane having a central inflatable bag and two opposing end cuffs, one of said end cuffs being mounted over the second reduced section with the outer end face of said one end cuff facing a shoulder separating the first and second reduced sections, said other end cuff being mounted over the first reduced section with the outer end face of said other end cuff facing a second shoulder separating the first reduced section and said body so that the inflatable bag is everted over the said one end cuff to enclose the first reduced section, a first adhesive bonding means for joining the end cuffs to the reduced sections and a second thermal bonding means formed by shrinkage of said cuffs and expansion of said catheter body section whereby the cuffs are double bonded to the catheter body; an inflation port formed in the wall of said first reduced section, and an air lumen mounted inside said body that is connected to the inflation port whereby the inflatable bag can be inflated and deflated.

2. The balloon catheter of claim 1 wherein said second reduced section forms the tip of the catheter at the distal end thereof.

3. The balloon catheter of claim 2 that further includes a service lumen mounted inside the body that has an opening at the distal end face of the body section.

4. The balloon catheter of claim 1 wherein the diameter of the first reduced section is such that the inflatable bag of the balloon is below the outer surface of the body when the bag is stored in a deflated condition.

5. The balloon catheter of claim 1 wherein the adhesive bond is formed using a cyanoacrylate adhesive.

6. A method of manufacturing a balloon catheter that includes the steps of forming a first reduced diameter section and a second smaller diameter second reduced section in a cylindrical polyethylene catheter body so that the sections are positioned adjacent each other, connecting an internal lumen to an inflation port that passes through the wall of the first reduced section, forming a thin walled tube of thermosetting polyurethane into a balloon having an inflatable bag centered between a pair of opposed end cuffs, applying an adhesive to a portion of said second reduced section, positioning one of said cuffs over the second reduced section so that the end face of the cuff is facing a shoulder formed between the two reduced sections, permitting the adhesive to dry, turning the balloon back over the bonded cuff, and applying an adhesive to a portion of said first reduced section, positioning the opposing cuff over the first reduced section with the end face of the second cuff facing a second shoulder formed between the body and the first reduced section so that the inflatable bag encircles the inflation port in the first reduced section and is retractable to a position below the outside surface of said body section when the bag is in a deflated condition heating the cuffs and the catheter body sections covered by said cuffs to a temperature at which the polyurethane shrinks and the polyethylene expands to form a thermal bond therebetween whereby said balloon is double bonded to said catheter body.

7. The method of claim 6 that includes the further steps of locating the second reduced section at the distal end of the catheter to form an axially disposed tip thereon, and extending the said one cuff outwardly beyond the distal end of the catheter.

* * * * *